United States Patent
van Steenwinckel et al.

(10) Patent No.: US 8,994,194 B2
(45) Date of Patent: Mar. 31, 2015

(54) SEMICONDUCTOR DEVICE HAVING AU—CU ELECTRODES, AND METHOD OF MANUFACTURING SEMICONDUCTOR DEVICE

(71) Applicant: NXP B.V., Eindhoven (NL)

(72) Inventors: David van Steenwinckel, Holsbeek (BE); Thomas Merelle, Leuven (BE); Franciscus Petrus Widdershoven, Eindhoven (NL); Viet Hoang Nguyen, Leuven (BE); Dimitri Soccol, Heverlee (BE); Jan Leo Dominique Fransaer, Leefdaal (BE)

(73) Assignee: NXP, B.V., Eindhoven (NL)

( * ) Notice: Subject to any disclaimer, the term of this patent is extended or adjusted under 35 U.S.C. 154(b) by 0 days.

(21) Appl. No.: 14/171,975

(22) Filed: Feb. 4, 2014

(65) Prior Publication Data
US 2014/0159173 A1      Jun. 12, 2014

Related U.S. Application Data (62) Division of application No. 13/568,695, filed on Aug. 7, 2012, now Pat. No. 8,679,966.

(30) Foreign Application Priority Data

Aug. 12, 2011   (EP) .................................. 11177456

(51) Int. Cl.
*H01L 21/02*   (2006.01)
*H01L 29/66*   (2006.01)
(Continued)

(52) U.S. Cl.
CPC ........ *G01N 27/4145* (2013.01); *G01N 27/3275* (2013.01); *H01L 29/66* (2013.01)

USPC ........................... 257/778; 257/548; 257/558

(58) Field of Classification Search
USPC ........................................... 257/548.558, 778
See application file for complete search history.

(56) References Cited

U.S. PATENT DOCUMENTS 7,045,389 B1   5/2006   Tatsumi et al.
7,304,831 B2   12/2007   Yoshii et al.
(Continued)

FOREIGN PATENT DOCUMENTS

CN   1822263 A   8/2006
CN   101634032 A   1/2010
(Continued)

OTHER PUBLICATIONS

Tai, C.-Y. et al. "Preparation and Characterization of an $AuCu_3$ Alloy Electrode for Electrocatalytic Applications", Electrochimica Acta, vol. 56, No. 9, pp. 3115-3121 (Jan. 2011).
(Continued)

*Primary Examiner* — James Mitchell (57) ABSTRACT

A method of manufacturing a biosensor semiconductor device in which copper electrodes at a major surface of the device are modified to form Au—Cu alloy electrodes. Such modification is effected by depositing a gold layer over the device, and then thermally treating the device to promote interdiffusion between the gold and the electrode copper. Alloyed gold-copper is removed from the surface of the device, leaving the exposed electrodes. The electrodes are better compatible with further processing into a biosensor device than is the case with conventional copper electrodes, and the process windows are wider than for gold capped copper electrodes. A biosensor semiconductor device having Au—Cu alloy electrodes is also disclosed.

4 Claims, 4 Drawing Sheets

(51) Int. Cl.
*H01L 29/40* (2006.01)
*G01N 27/414* (2006.01)
*G01N 27/327* (2006.01)

(56) References Cited

U.S. PATENT DOCUMENTS

| | | | |
|---|---|---|---|
| 7,863,188 B2 | 1/2011 | Tsurume et al. | |
| 7,902,717 B2 | 3/2011 | Saijou et al. | |
| 2009/0184002 A1 | 7/2009 | Furukawa et al. | |
| 2011/0068656 A1* | 3/2011 | Lee et al. | 310/313 C |
| 2012/0105174 A1* | 5/2012 | Lee et al. | 333/193 |

FOREIGN PATENT DOCUMENTS

| | | |
|---|---|---|
| CN | 101950771 A | 1/2011 |
| GB | 1 203 594 | 8/1970 |
| WO | 2007/125479 A2 | 11/2007 |
| WO | 2008/041404 A1 | 4/2008 |

OTHER PUBLICATIONS

Extended European Search Report for EP Patent Appln. No. 11177457.6 (Nov. 22, 2011).

* cited by examiner

SEMICONDUCTOR DEVICE HAVING AU—CU ELECTRODES, AND METHOD OF MANUFACTURING SEMICONDUCTOR DEVICE

CROSS-REFERENCE TO RELATED APPLICATIONS

This application is a divisional of copending U.S. patent application Ser. No. 13/568,695, filed on Aug. 7, 2012.

This application claims the priority under 35 U.S.C. §119 of European patent application no. 11177457.6, filed on Aug. 12, 2011, the contents of which are incorporated by reference herein.

FIELD OF THE INVENTION

This invention relates to semiconductor devices which are compatible with CMOS processing and methods of manufacturing the same. In particular it relates to semiconductor devices which are further processable to become biosensors and to methods of manufacturing biosensors.

BACKGROUND OF THE INVENTION

Recently, bio-sensing devices have been developed which include a semiconductor device based on advanced CMOS processing techniques. Conventional biosensing devices typically rely on inert metals, such as gold or platinum, for their electrodes, in order to provide a high level of compatibility with the often corrosive, or otherwise oxidising, environments in which such biosensors may be used, or which may be required for downstream or subsequent processing of the semiconductor device; however, there has been a recent move towards copper electrodes, in order to maximise the compatibility with standard CMOS processing steps and equipment. However, copper is known to suffer from oxidisation and corrosion under conditions where biosensors are used.

A biosensor device is known from United States Patent Application publication number US2009/184,002, which includes at least one electronic element having a metal electrode which may be made from copper or an alloy comprising copper. US2009/184,002 teaches that, whereas in general in biosensor devices noble metals such as gold silver and platinum are used it is preferable to use copper, since this is compatible with advanced semiconductor processing. The copper readily oxidises to form CuxOy, which may then be cleaned later in the processing, in particular in preparation for the application of a self assembled monolayer, which may then act to protect the electrodes from corrosion and to couple biomolecules on top.

It would be desirable to provide a semiconductor device, and a method of manufacturing semiconductor device, which combines the advantages of copper-based electrode technology within the semiconductor device, and inert metal-electrodes for later processing as a biosensing device.

SUMMARY OF THE INVENTION

It is an object of the present invention to provide a semiconductor device, and a method of manufacturing a semiconductor device, which are compatible with advanced CMOS processes and with further processing as a biosensor for biosensing applications.

According to the invention there is provided a method of manufacturing a biosensor semiconductor device having Au—Cu alloy electrodes at a major surface thereof, the method comprising: providing the semiconductor device with Cu electrodes at the major surface and extending into the device; depositing a Au layer over the Cu electrodes; thermally treating the semiconductor device to alloy deposited Au and the Cu electrodes, thereby forming the Au—Cu alloy electrodes, and polishing the semiconductor device to expose the Au—Cu alloy electrodes.

By providing, in the first place, copper electrodes, compatibility with CMOS processing, either standard CMOS processing or advanced CMOS processing, may be maintained. Moreover, by limiting the amount of free copper at the surface (for instance, as would be the case by providing a capping layer of gold) the problems of oxidation of exposed copper, which occur with conventional biosensor devices having copper electrodes, may be alleviated. Beneficially, according to embodiments, there is no requirement for a photolithography step to align the gold deposition with the electrodes. This is particularly beneficial in applications in which the electrodes are microelectrodes such that the lateral dimensions of the electrodes are microns, or nano-electrodes such that the dimensions of the electrodes are less than one micron. Thus the gold deposition need not be limited to being only over the copper electrodes. That is to say, the gold layer may be deposited over and beyond the copper electrodes. It will be appreciated that the provision of copper electrodes need not include their isolation and/or separation; in particular, a copper layer may be deposited which includes the copper electrodes and a subsequent chemical mechanical polishing step may or may not be performed to remove copper from other parts of the surface.

Furthermore, it will be appreciated that, in contrast to conventional metallisations involving deposition of gold over copper, no barrier layer, such as Ti is required, since intermixing of the gold and copper is, in the present instance, necessary, rather than to be prevented by a barrier layer.

In embodiments, thermally treating the semiconductor device to alloy deposited Au and the Cu electrodes comprises completely alloying the Cu electrodes. By consuming the copper into specific $Au_xCu_y$ compounds, the copper is "fixed" in the sense that it is no longer able to migrate to the surface of the electrode or to corrode or form oxides. It will be appreciated that all or part of the deposited Au may be alloyed, depending on the specific conditions used. In embodiments, a thickness of the deposited Au layer is at least 50 nm. Such a thickness of the deposited layer of gold is typically sufficient to ensure there is an excess of gold in order to allow all the copper to be consumed, that is to say fixed in specific $Au_xCu_y$ compounds. It will be appreciated that a thinner layer, for instance of only 10 nm, may be possible; however, to achieve such a thin layer would generally require an inconvenient thermal budget, such as an inappropriately long annealing time.

In embodiments, polishing the semiconductor device comprises chemical-mechanical polishing. Alternatively, other polishing techniques, though generally less well-developed in the industry, may be used: for instance and without limitation, purely mechanical polishing or electropolishing, wherein the device is polished by the application of an electric field, inversely analogous to electroplating, may be used to remove the unwanted metal.

In embodiments, thermally treating the semiconductor device comprises heating the semiconductor device to a temperature which is within 50° of either 350° C. or 450° C. for a time which is within 15 minutes of one hour. These thermal treatments have been experimentally shown to provide sufficient alloying of the gold and copper to result in a high level of corrosion resistance.

Since the concentration of copper in the alloy may vary across the device, with typically a higher level of copper above the electrodes than elsewhere, it is preferable that the CMP step is carried out using a slurry which balances the polishing rate of gold and copper. For example a copper-protecting agent may be added to a gold-CMP slurry in order to reduce any acceleration of the polishing above the electrodes due to a higher concentration of copper relative to elsewhere on the device.

In embodiments, the Cu electrodes comprise the final metal layer of a multilevel Damascene metallisation stack. Due to the multi-level arrangement of a Damascene metallisation stack, migration of gold close to the active CMOS areas of the semiconductor device, which may be deleterious to the operation of the device, may be limited. In embodiments, the semiconductor device comprises silicon or a silicon-containing material. Silicon-based material systems are particularly suited for commercial biosensor applications, since they are the most widely developed among semiconductor material systems.

The method may further comprise depositing a self-assembled-monolayer on the exposed Au—Cu alloy electrodes.

It may further comprise a preceding step of separating the semiconductor device from a wafer. Thus the invention is not limited to with the state processing that may be carried out at a device level.

In embodiments, the electrodes have dimensions of no more than one micrometer in lateral directions at the major surface of the semiconductor. In embodiments, the biosensor is adapted for capacitive sensing, and the Au—Cu alloy electrodes comprise sensing electrodes.

According to another aspect of the invention, there is provided a biosensor semiconductor device having Au—Cu alloy electrodes at a major surface thereof and extending into the device. Au—Cu electrodes have proven particularly beneficial in avoiding limiting corrosion of the surface of the electrode, and thereby enhancing the adsorption or chemisorption of deposited materials such as self assembled monolayers for use in association with or as bioreceptors in biosensing applications.

In embodiments, the electrodes have a relatively Au-rich composition at the major surface of the device, and a relatively Cu-rich composition further from the major surface. Having a relatively Au-rich composition at major surface helps to avoid corrosion at the surface; having relatively Cu-rich composition further from the major surface may assist in limiting the subsequent diffusion of gold towards the active areas of the device. In embodiments, the electrodes have dimensions of no more than one micrometer in lateral directions at the major surface of the semiconductor. Such embodiments are compatible with massively parallel capacitive-based biosensing devices. In embodiments, the lateral spacing between adjacent electrodes is at least four times the width of adjacent electrodes.

These and other aspects of the invention will be apparent from, and elucidated with reference to, the embodiments described hereinafter.

BRIEF DESCRIPTION OF DRAWINGS

Embodiments of the invention will be described, by way of example only, with reference to the drawings, in which FIGS. 1($a$) to 1($c$) show schematic diagrams of a semiconductor device at three stages of a method of providing a semiconductor device according to embodiments.

It should be noted that the Figures are diagrammatic and not drawn to scale. Relative dimensions and proportions of parts of these Figures have been shown exaggerated or reduced in size, for the sake of clarity and convenience in the drawings. The same reference signs are generally used to refer to corresponding or similar feature in modified and different embodiments.

DETAILED DESCRIPTION OF EMBODIMENTS

Figures 1A, 1B, 1C:
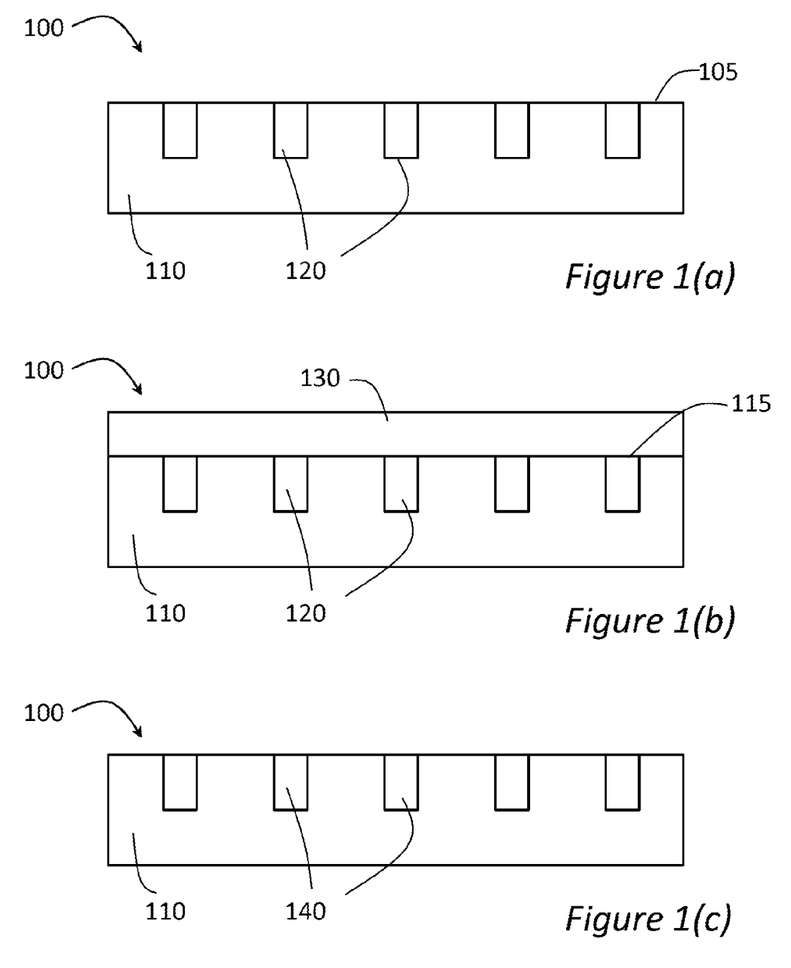
Figure 2:
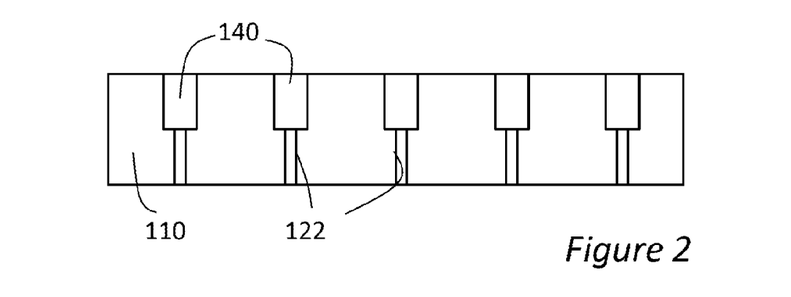
FIG. 2 shows a cross-section of part of a semiconductor device having a Damascene multilayer metallisation.

FIGS. 1($a$) to 1($c$) show schematic diagrams of a semiconductor device at three stages of a method of providing a semiconductor device according to embodiments. FIG. 1($a$) shows a schematic cross-section through a semiconductor device 100, being a major surface 105, and including the copper electrodes 120 at the major surface and extending into the semiconductor device. Within the body 110 of semiconductor device are various regions, layers and features associated with either standard or advanced CMOS processing. Up to this stage of its manufacturer, the device is entirely compatible with standard or advanced CMOS processes.

FIG. 1($b$) shows the semiconductor device 100, following the deposition of a gold layer 130 on the major surface of the device. As shown in FIG. 1, the gold layer is deposited generally across the device, that is to say there is no photolithography, or other masking the stage required to limit the deposition of the gold to being only over the copper electrodes. The gold layer 130 may be relatively thick, or the copper electrodes relatively widely spaced, such that, compared to the volume of copper in the copper electrodes, there is a higher volume of gold deposited on the device. Sputtering is a particularly convenient deposition method for the gold layer 130. However, alternative types of vacuum deposition such as evaporation may be used. It is noted that the invention is not limited thereto, and yet other ways providing a gold layer on the surface of the semiconductor device (for instance by electroplating) may also be used.

In the next stage of the process, (not shown), the semiconductor device is subjected to a thermal treatment in order to promote the alloying of the gold layer 130 with a copper electrodes 120. Specific alloying conditions may vary depending on the individual device and the thicknesses of the layers used; however it has been found that heating the semiconductor device to within 50° of 350° C. for between 45 min and 1 hour 15 min, and particularly heating the semiconductor device to 350° C. for 1 hour, may provide a suitable degree of alloying of the copper and gold. In other experiments it has been found that heating the semiconductor device to within 50° of 450° C. for between 45 min and 1 hour 15 min, and in particular heating the semiconductor device to 450° C. to for 1 hour also provides a suitable amount of alloying of the copper and gold, although in this case, the specific AuCu compounds and phases formed are different, to those formed at or around 350° C.

Figure 3:
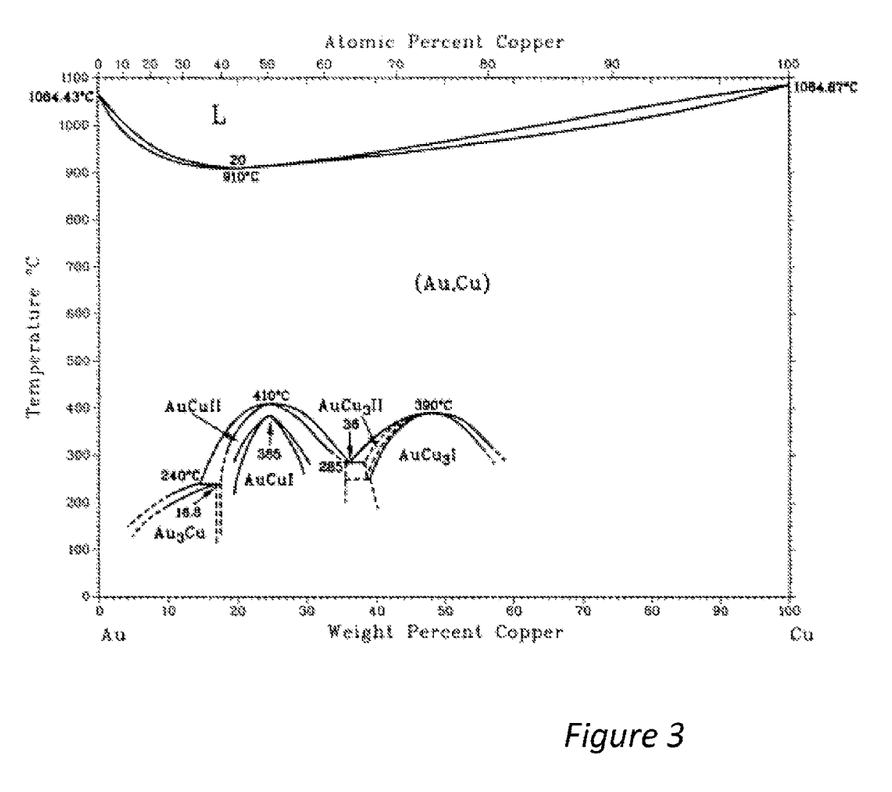
FIG. 3 shows a Au—Cu phase diagram.

The skilled person will appreciate that the phase diagram of copper gold is nontrivial, and that diffusion of the two metals can occur even at room temperature. A phase diagram of copper and gold is shown in FIG. 3. In general, the copper out-diffuses into the gold, and the gold in-diffuses into the copper. From the figure it may be seen that an Au—Cu alloy can include several specific compounds, for example $AuCu_3$, which can exist in two crystallographic phases, $Au_3Cu$ which exists in a single crystallographic phase, and AuCu which can also exist in two crystallographic phases. Furthermore, in a relatively Au-rich composition there may be solid solution of gold within the matrix of a specific $Au_xCu_y$ compound; conversely in a Cu-rich environment there may be solid solution of copper within the matrix of a specific $Au_xCu_y$ compound.

Advantageously, all of the copper in the copper electrodes 120 may be consumed forming one or more specific copper-gold $Au_xCu_y$ compounds such as $Au_3Cu$, $AuCu_3$, and AuCu. Even if all the copper is not consumed, the excess of gold which is available for the alloying process due to the relatively thick deposited gold layer may provide that there is a relatively low or even negligible amount of free copper (that is to say copper which is in a solid-state solution rather than in a specific alloy phases such as $Au_3Cu$) at the surface of the gold layer at the end of the thermal treatment. Typically, to provide good corrosion resistance, which is stable over time, a certain minimum ratio of gold to copper atoms the top of the electrode and no compositional gradient over the several atomic layers, such as for instance, the top 50 nm of the electrode, may be required. Furthermore, the excess of gold which is available for the alloying process due to the relatively thick deposited gold layer may provide that there is a relatively low or even negligible amount of free copper (that is to say copper which is in a solid solution rather than in a specific alloy phases such as $Au_3Cu$) at the top of the electrodes—i.e. at the major surface 105 of the semiconductor device.

Preferably the thermal treatment is carried out in a reducing atmosphere, such as forming gas, which has a composition of 5% $H_2$ and 95% $N_2$, in order to avoid or limit oxidation of any exposed copper. It has further been found beneficial to ensure that the samples are allowed to cool to at most 100° C. whilst remaining in the reducing atmosphere.

At a following stage of processing, the semiconductor device is planarised by CMP (chemical-mechanical polishing), to remove the excess gold from the semiconductor device. At the end of the CMP step, the semiconductor device is as shown in FIG. 1(*c*). It will be appreciated that this figure is similar to that shown in FIG. 1(*a*); however, the original copper electrodes 120 extending from the major surface into the semiconductor device are now replaced by Au—Cu alloy electrodes 140. It will be appreciated that which specific alloy phase or phases of the alloyed copper electrodes is or are present is less critical than that there is a relatively low level of free copper at the surface 115 of the electrode at the major surface of the semiconductor device. Preferably, the surface of the electrode comprises less than 2% free copper, and ideally no free copper at all.

The skilled person will be aware that the efficiency and uniformity of CMP depends heavily on the choice of polish compound or slurry used. In the present case, beneficially the entire surface is covered with Au-based material (gold, gold compounds or a solid-state solution of copper in gold), and the slurry should be chosen appropriately. An example of a suitable slurry is UltraSol A15 (supplied by Eminess) Advantageously, when compared to an un-alloyed gold capping layer, the CMP planarisation is much more uniform, and does not suffer to the same extent from the effects of dishing which can occur with CMP of gold. "Dishing" can occur when a soft material such as gold is CMP polished, adjacent to a harder material, such as SiOx or other dielectric materials typically present at the surface of a semiconductor device. Uniform polishing is easier to achieve with harder materials such as Au—Cu alloys.

Experimentally, it has been found that, addition of a copper-protecting agent (such as BTA, that is 1,2,3-Benzotriazole) into a gold-CMP slurry such as UltraSol A15 has been found to improve the uniformity of the CMP process: since the Cu concentration over the electrodes is generally higher than that over the remainder of the device, it has surprisingly been observed that gold-slurries may have a higher polishing rate above the electrodes and over the remainder of the device. This suggests that copper dissolution is a significant mechanism in the gold CMP process; experimentally it has been verified that inclusion of a copper-protecting agent can significantly improve the planarisation uniformity.

The skilled person will readily appreciate that, since the CMP step should stop at the surface of the semiconductor device, a CMP slurry should preferably be one which has as high selectivity against dielectrics such as silicon nitride or silicon oxide.

Dishing is particularly problematic where there are large electrodes (such as bond pad electrodes). Towards the end of the CMP, since the gold at the bond-pad is removed much more easily than the relatively hard material or materials (typically an oxide or other dielectric material) at other positions on the surface of the semiconductor device, the gold is preferentially polished away, leading to a relatively low surface, or "dish", in the bond pad area relative to the remainder of the surface. Whereas this effect is particularly significant for larger bond pads, it also can occur to a lesser extent at other electrodes, such as nanoelectrodes with lateral dimensions of less than a micron, which may typically be used, in a large array, for biosensor applications.

If a gold capping layer were to be used absent a thermal alloying treatment, then in subsequent CMP, it has been observed experimentally that the underlying copper of the original electrode may be exposed, particularly towards the central area of bond-pads. This may lead to further problems, such as the creation of an electrochemical cell between the gold and copper resulting in fast erosion and corrosion of the copper.

Furthermore, for CMP of gold-copper alloys, advantageously, water-based slurries may be used rather than the nonconductive slurry such as IPA (iso-propyl-alcohol) containing cerium oxide particles which are required for CMP polishing of pure gold. Water-based slurries may be less expensive and more environmentally friendly compared with those based on other solvents such as IPA. Thus the process window for CMP according to embodiments is much wider than would be the case for pure gold.

In other embodiments, other polishing techniques, such as purely mechanical polishing, may be used instead of chemical-mechanical polishing.

Figure 4:
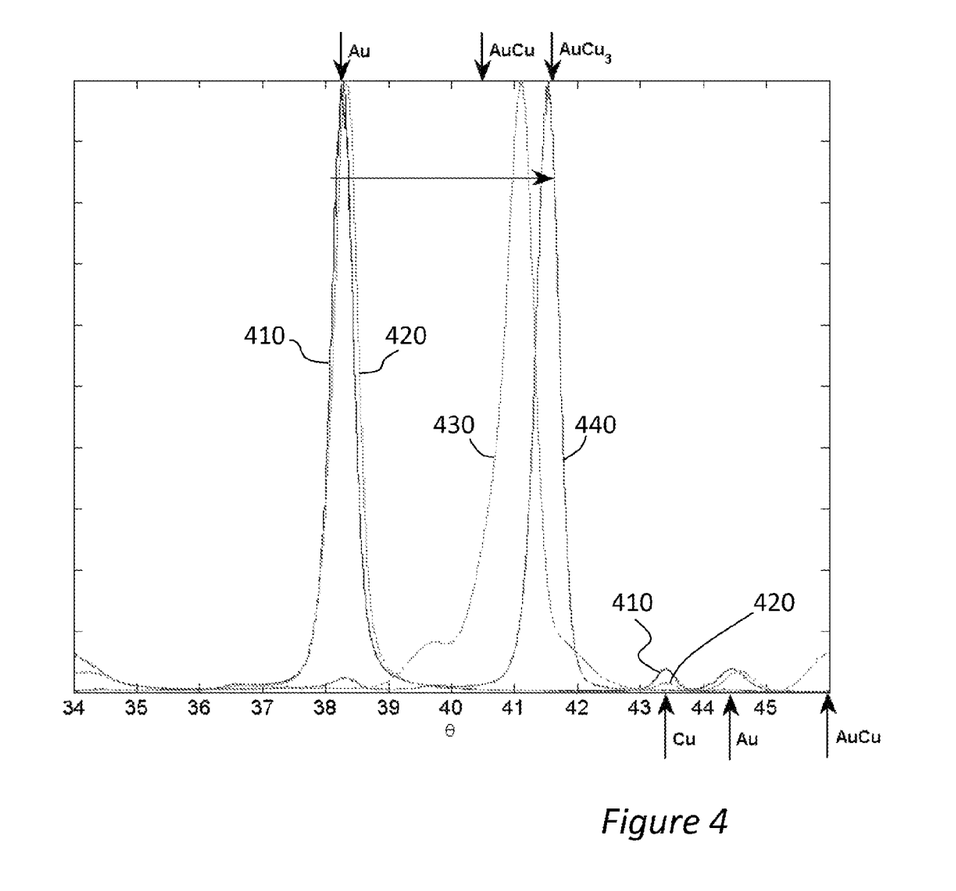
FIG. 4 shows XRD analysis of Au—Cu layers before and after thermal treatment.

FIG. 4 shows experimental results for the alloying process. On the figure is plotted, in arbitrary units, x-ray diffraction (XRD) measurements of the composition of the gold and copper electrodes, before heat treatment at curve 410, and after heat treatment, for two and half hours at 250° C. and 350° C. at curves 420 and 430 respectively, and after one hour at 450° C., at curve 440. As can be seen from the figure, the curves for the untreated electrodes, and the electrodes heated to 250° C. for two and half hours both show significant peaks for elemental gold (at 450 and 452), and for elemental copper (at peak 454). In contrast, in the curves 430 and 440 following heat treatment at high temperatures, these peaks have almost completely disappeared; instead, there is a noticeable peak at the position for AuCu in the case of curve 430, and for $AuCu_3$ in the case of curve 440. These experimental results demonstrate that elemental copper in particular has been consumed in the alloying process. Since the gold-copper alloys are far less susceptible to corrosion, that is to say oxidation, than elemental copper, the resulting electrode surface is more stable and compatible with good adhesion of, for instance, self assembled monolayers such as may be used in further processing of a biosensor device.

Further experimental analysis of the surface composition of the electrodes following the alloying step and planarisation by CMP, have demonstrated that after an alloying step of one hour at 350° C., the surface contains 43±3 atomic percent of gold, and after an alloying step of one hour at 450° C., the surface contains 35±1 atomic percent of gold.

Experimentally, improved corrosion protection relative to bare copper electrodes has been demonstrated by using corrosion tests in a physiological buffer. In particular a 150 mM chloride containing salt has been applied, as well as 10 mM glycine solutions acidified to a pH level of 2: the CMP gold-copper alloy electrode reveals relatively less corrosion; in one case no visible damage was been observed by SEM after 30 minutes in 10 mM glycine solution or after 4 hours in 150 mM chloride solutions.

Figure 5:
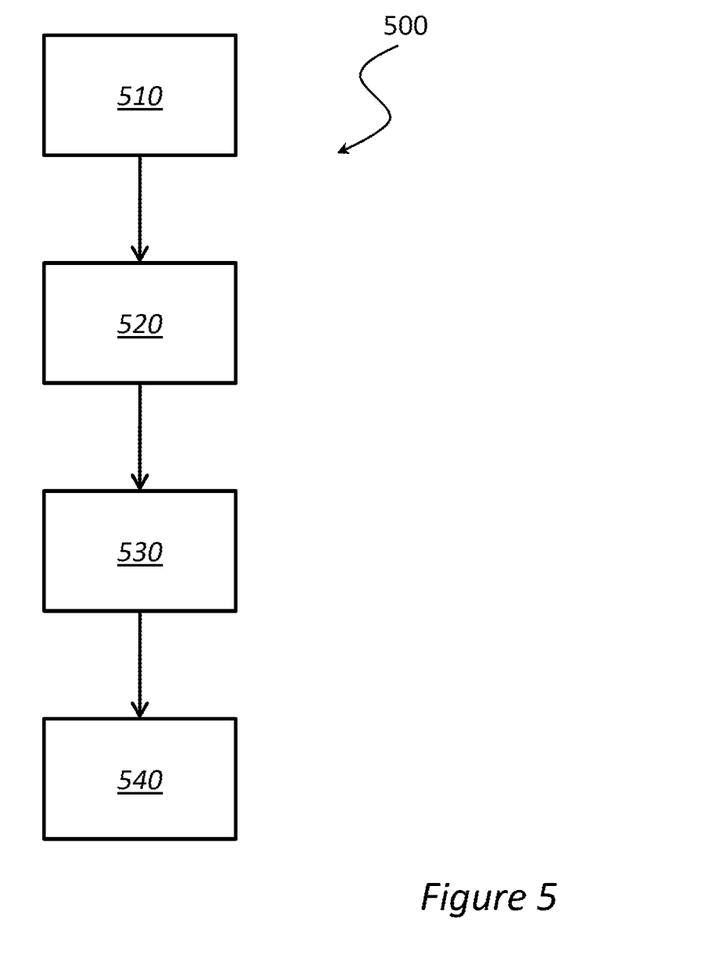
FIG. 5 shows a flow diagram according to embodiments.

FIG. 5 shows a flow diagram 500 according to embodiments. Semiconductor device 100 is provided, at step 510, with copper electrodes at its major surface and extending into the device. Up to this stage, the processing of the devices may be entirely conventional. Thereafter, at step 520, the gold layer is deposited over the device. The deposition of the gold is not limited to being over just over the copper electrodes; thus no photolithography step involving accurate alignment to the electrodes is required. It should be noted that although the gold deposition is not limited to being over the copper electrodes, it is not necessary that the gold is deposited over the entire device. Furthermore, the deposition may be done at a device level, that is to say after individual devices have been separated from the processed semiconductor wafer; however, in general it will be the case that the gold deposition occurs at the wafer level, that is to say before the wafer is separated into individual devices or dice.

Next, at step 530 the die or wafer is subjected to a thermal treatment, typically in a reducing atmosphere, in order to promote the interdiffusion of the copper and gold to produce a gold-copper alloy. Whilst copper may diffuse laterally or up from the major surface, gold from the deposited gold layer diffuses into the copper electrode and down or into the device away from the major surface. Due to the relative excess of gold, which typically results from the deposited gold layer not being constrained to being only over the copper electrodes, the copper from the electrodes may be significantly or entirely consumed or take up in the alloy, whereas the gold typically is not.

Thereafter, at step 540, the device, or the wafer in the case that the depositions and alloying is carried out at a wafer level, is chemical mechanically polished, in order to remove the remaining excess gold, which will typically have been at least partially converted to a gold-copper alloy, from the device except at the electrodes. The alloyed gold-copper electrodes are thereby exposed.

In the above mentioned process flow, it is assumed that the biosensor semiconductor device has been processed conventionally, up to the stage where the only exposed copper at the major surface is at the electrodes. That is to say, the fabrication of convention electrodes is complete. However, in other embodiments, the process may be slightly different: in a typical process to produce the top copper electrodes, such as Damascene, the metal, in this case copper, is deposited across the complete device, including into preformed partial vias. (By partial vias is meant vias which extend from the major surface into the device, but generally not completely through the device). In conventional processing, the device is then planarised by CMP in order to remove metal from unwanted areas and retain metal only in the partial vias. In embodiments, the copper layer is not planarised, rather, after depositing this layer, the gold layer 130 is deposited at step 520. In other words, relative to the above-described process flow, step 510 is modified in that it does not include any CMP planarisation of the copper. The process then proceeds as described above, with the difference that the gold interdiffuses into the copper not just at the electrodes but across the whole device. To provide the preferred gold excess, a relatively thicker layer of gold must be deposited, when compared with the process flow described above. However, this modified process flow has the advantage that the interdiffusion between gold and copper is much more uniform across device, which may result in a wider process window for the subsequent CMP stage 540.

Seen from one perspective, then, there is disclosed herein a method of manufacturing a biosensor semiconductor device, in which copper electrodes at the major surface of the semiconductor devices are modified to form Au—Cu alloy electrodes. The modification is effected by depositing, typically by sputtering, a gold layer over the device, and then thermally treating the device to promote interdiffusion between the gold and the electrode copper and to alloy them. The alloyed gold-copper is removed from the surface of the device typically by CMP, leaving the exposed electrodes. Since the gold-copper alloy is harder than gold, the CMP process window is wider than would be the case of pure gold; moreover, since the electrode copper has been converted to a gold-copper alloy, it is more corrosion resistant than a conventional copper electrode. The electrodes are thus better compatible with further processing into a biosensor device than is the case with conventional copper electrodes, and the process windows are wider than for gold capped copper electrodes. A biosensor semiconductor device having Au—Cu alloy electrodes is also disclosed.

As will be appreciated by the skilled person, the term "biosensor" as used here in denotes a sensor which is capable of sensing biologically active molecule or complex. Biologically active molecules are typically large, organic molecules.

From reading the present disclosure, other variations and modifications will be apparent to the skilled person. Such variations and modifications may involve equivalent and other features which are already known in the art of biosensing semiconductor devices, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub-combination.

The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, and reference signs in the claims shall not be construed as limiting the scope of the claims.

The invention claimed is:

1. A biosensor semiconductor device having Au—Cu alloy electrodes at a major surface thereof and extending into the device, wherein the electrodes have a relatively Au-rich composition at the major surface of the device, and a relatively Cu-rich composition further from the major surface.

2. A biosensor semiconductor device as claimed in claim 1, wherein the electrodes have dimensions of no more than one micrometer in lateral directions at the major surface of the semiconductor.

3. A biosensor semiconductor device as claimed in claim 1, wherein the lateral spacing between adjacent electrodes is at least four times the width of adjacent electrodes.

4. A biosensor semiconductor device as claimed in claim 1, wherein the biosensor is adapted for capacitive sensing, and the Au—Cu alloy electrodes comprise sensing electrodes.

* * * * *